(12) United States Patent
Gjersøe (10) Patent No.: US 6,216,702 B1
(45) Date of Patent: *Apr. 17, 2001

(54) INTERNAL REGISTRATION OF GAS/AIR— AND OTHER FLUID FLOWS IN A HUMAN BODY AND USE OF PRESSURE SENSORS FOR SUCH REGISTRATION

(75) Inventor: Bjørn G. Gjersøe, Høvik (NO)

(73) Assignee: Camtech AS, Høvik (NO)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/864,787

(22) Filed: May 29, 1997

Related U.S. Application Data

(63) Continuation of application No. PCT/NO95/00230, filed on Dec. 12, 1995.

(30) Foreign Application Priority Data

Dec. 14, 1994 (NO) .................................................. 944844

(51) Int. Cl.$^7$ ..................................................... A61B 19/00
(52) U.S. Cl. ............... 128/898; 128/200.24; 128/205.23; 600/532; 600/538
(58) Field of Search ..................................... 128/897, 898, 128/200.24, 200.22, 205.23; 600/529, 532, 538

(56) References Cited

U.S. PATENT DOCUMENTS

| 3,672,352 | * | 6/1972 | Summers ................................. 128/2 |
| 3,961,626 | * | 6/1976 | Houchen et al. ................. 128/145 R |
| 4,554,927 | | 11/1985 | Fussell . |
| 4,938,212 | * | 7/1990 | Snook et al. ..................... 128/205.24 |
| 5,056,519 | * | 10/1991 | Vince .................................... 128/419 |
| 5,311,875 | | 5/1994 | Stasz . |
| 5,339,051 | * | 8/1994 | Koehler et al. .......................... 331/65 |
| 5,540,220 | * | 7/1996 | Gropper et al. ................. 128/204.23 |
| 5,680,871 | * | 10/1997 | Ganshorn ............................ 128/720 |
| 5,833,603 | * | 11/1998 | Kovacs et al. ......................... 600/317 |
| 5,836,989 | * | 11/1998 | Shelton ................................. 607/27 |

FOREIGN PATENT DOCUMENTS

| 57746/94 | 9/1994 | (AU) . |
| 0 046 570 | 3/1982 | (EP) . |
| 0 392 897 | 10/1990 | (EP) . |
| 1 313 486 | 4/1973 | (GB) . |
| 377 276 | 6/1975 | (SE) . |
| 377276 | 6/1975 | (SE) . |

OTHER PUBLICATIONS

Cranen, et al. "Pressure measurements during speech production using semiconductor miniature pressure transducers: Impact on models for speech production." *J. Acoust. Soc. Am.* 77(4), Apr. 1985. pp. 1543–1551.

(List continued on next page.)

*Primary Examiner*—Dinh X. Nguyen
(74) *Attorney, Agent, or Firm*—Merchant & Gould P.C.

(57) ABSTRACT

A method for internal registration of the flow of a fluid into, in or out of a living body wherein one or a series of sensors are placed at one or more points along the flow path of the fluid and the registration takes place through the utilisation of the sensor's or sensors' inherent, pressure and/or temperature—dependent physical and electrical properties, by measuring the temperature and the difference in temperature in the flowing fluid.

5 Claims, 3 Drawing Sheets

OTHER PUBLICATIONS

Mosse, et al. "Microprocessor–based time–of–flight respirometer." *Medical & Biological Engineering & Computing*, Jan. 1987. pp. 34–40.

Isabey, et al. "Dependence of central airway resistance on frequency and tidal volume: a model study."*The American Phsiological Society*, 1986. pp. 113–126.

Chaban, et al. "Site of upper airway obstruction in patients with idiopathic obstructive sleep apnea." Reprint from *Laryngoscope*, vol. 98, No. 6, Jun. 1988. pp. 641–647.

Tvinnereim, et al. "Pressure recordings—A method for detecting site of upper airway obstruction in obstructive sleep apnea syndrome." *Acta Otolaryngl* (*Stockh*), Suppl. 492, 1992. pp. 132–140.

* cited by examiner

INTERNAL REGISTRATION OF GAS/AIR— AND OTHER FLUID FLOWS IN A HUMAN BODY AND USE OF PRESSURE SENSORS FOR SUCH REGISTRATION

This is a continuation of PCT/NO95/00230 application filed Dec. 12, 1995.

FIELD OF THE INVENTION

The present invention relates to a method for internal registration of the flow of a fluid into, in or out of a living body.

SUMMARY AND BACKGROUND OF THE INVENTION

The invention relates especially to a method for the registration of respiration in human beings, preferably during sleep.

The invention also relates to the use of pressure-sensitive sensors that are known per se for the registration of temperature in connection with the aforementioned method.

Although the invention is described primarily in connection with measuring respiration during sleep, the principal idea of the invention could also be used during registration in connection with the flow and/or leakage of urine, the flow of blood and so forth.

Sleep is a periodic and, as a rule, rhythmically occurring state in which physical and mental activity are diminished.

Sleep brings about an immobility which is energy-conserving, the body's metabolism slows down, the muscles relax, breathing and the action of the heart become slower, and blood pressure falls.

In this state, a new supply of energy is built up and stored, and sleep is therefore a condition of life for living creatures.

It is therefore of crucial importance that the quality of sleep is the best possible and that disturbances can be remedied.

Different types of obstructions in the airways are among the problems which may lead to disturbed sleep for an individual.

These obstructions may be so serious that, in addition to a purely physical disturbance of sleep, they can result in a reduction and eventual stoppage of the oxygen supply with the consequences this has for the action of the heart, the cardiovascular system and other organs, in the short term and the long term.

In addition to the problems this causes for the individual in question, a problem such as snoring is also a real family or social problem because of the disturbance snoring can cause for other people in the period of sleep necessary for each individual.

In the registration of sleep in patients suffering from so-called sleep apnea, ie, the temporary cessation of breathing, techniques have been established which aim to register inhalation and exhalation.

One of the ways in which this is done is by placing one or more temperature-sensitive sensors between the nose and the mouth of the patient so that the sensors are subjected to the effect of the air which is breathed in and out, such as is described, eg, in U.S. Pat. No. 5,311,875.

Since the temperature of the inhaled air is different to that of the exhaled air, it is possible by means of suitable measuring and registering equipment to produce the signal emitted by the sensor in the form of a graphical respiration curve.

Together with the measurement and presentation of a number of other physiological parameters such as, eg, ECG, oxygen levels in the blood, EEG, eye movements, where especially the last-mentioned gives a good indication of the stage of sleep reached, respiration is also an important parameter for the diagnosis of a patient's condition.

Recently, the use of pressure registration at several points in the respiratory passage has been introduced.

The measurement of the pressure variations at predetermined points in the respiratory passage makes possible the localisation of obstructions in the sleep period. Pressure registrations of this kind are carried out by means of so-called micro-sensor catheters, ie, fine plastic tubes into which are mounted small pressure sensors.

Pressure-related signals, from both direct and indirect pressure which is exerted on these sensors, are conveyed to the sleep registration equipment and produced as pressure curves, eg, on the screen of a personal computer.

Since pressure sensors of this kind are usually more or less temperature-sensitive by nature, it is essential that the effects of temperature be compensated so that temperature fluctuations have a minimal effect on the pressure signals.

Of the known technology in this field, reference shall be made to U.S. Pat. No. 4,554,927, which describes a pressure and temperature sensor based on a piezoresistant element, made of a silicon crystal. However, the device described in this publication is unsuitable for measuring fluid flows. An essential aspect of this device is that it measures temperature in a separate, temperature-sensitive part which, however, is not pressure-sensitive.

For a general description of technology in this field, reference shall also be to the international application, WO 93/19669.

In contrast to the prior art, the present invention aims to utilise the effects of temperature in pressure sensors that are known per se.

BRIEF DESCRIPTION OF THE DRAWINGS

The invention shall be explained in more detail with reference to the accompanying drawings wherein.

DETAILED DESCRIPTION OF PREFERRED EMBODIMENTS

Figure 1:
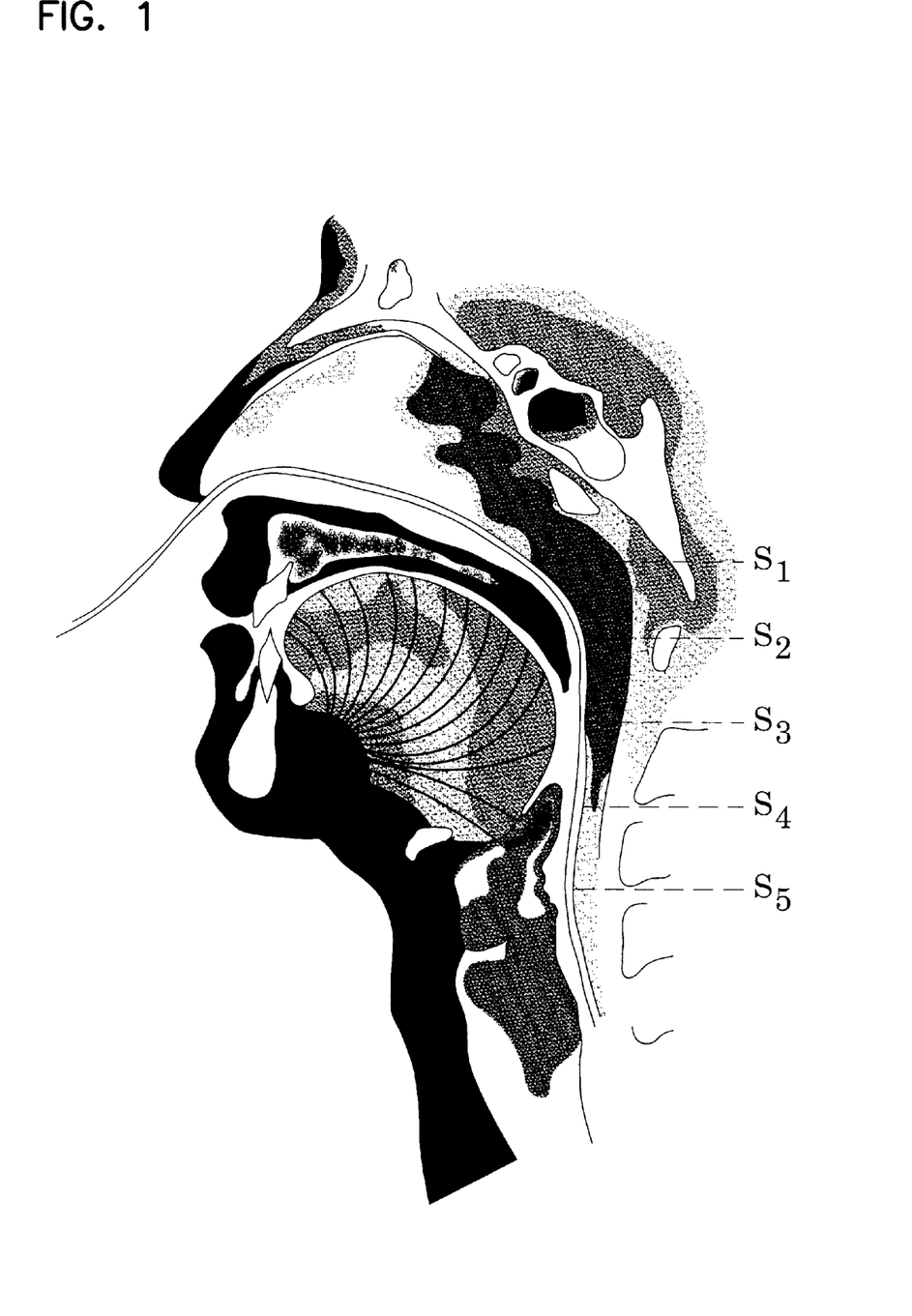
FIG. 1 illustrates internal pressure/temperature sensors in the flow path of the respiratory fluid.

The present invention is thus based on the utilisation of this temperature sensitivity in order to register a patient's inhalation and exhalation, ie, respiration, by means of temperature-sensitive sensors which are placed in one or more positions in the airway, such as is shown in FIG. 1 where five sensors are arranged in a fine, flexible tube.

In accordance with the above, the present invention relates to a method for registering the flow of a fluid inside, in or out of a living body, and this method is characterised in that one or a series of pressure-sensitive sensors are provided at one or more points along the flow path of the fluid and that registration takes place through the utilisation of the sensor's/sensors' inherent, temperature-dependent, physical and electrical properties, when measuring the temperature and difference in temperature in the flowing fluid.

As mentioned in the introduction, the invention also relates to the use of pressure-sensitive sensors that are known per se for in vivo measuring of the temperature and difference in temperature in fluids which flow into, in or out of a living body.

As stated above, the measurements can be taken in the urinary tract, in blood vessels and so forth, but the invention shall be described in more detail and will also have a special application in connection with the registration of the respiration of an individual, particularly during sleep.

Figure 2:
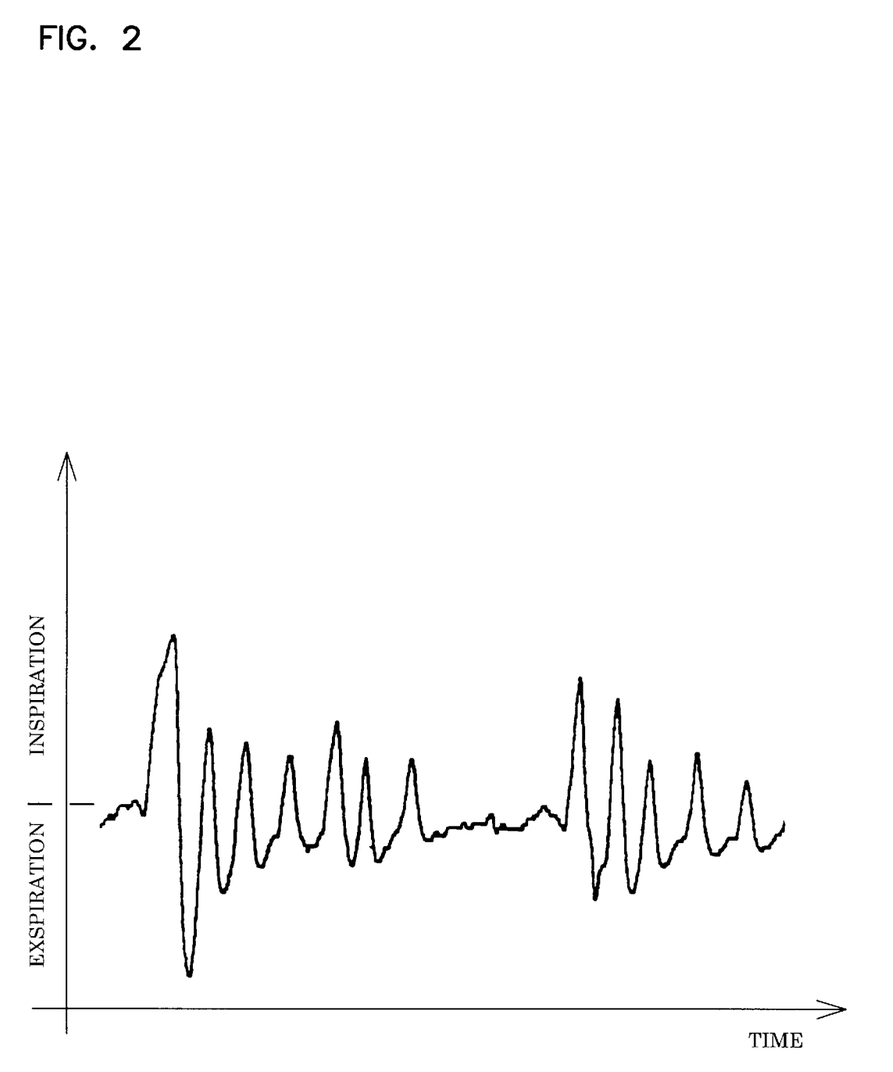
FIG. 2 shows the tidal volume signal of respiration with internal temperature registration.

FIG. 2 illustrates the registration of an individual's respiration during sleep and reproduces the tidal volume signal for inspiration and expiration with internal temperature registration.

In order to register the patient's respiration, the aforementioned temperature-sensitive sensors may, for example, be placed in a fine plastic tube in the same way as pressure sensors are mounted in a micro-tip-sensor catheter, see the illustration in FIG. 1.

The registration of respiration is based on the fact that the temperature of inhaled air is lower than that of exhaled air and that the quantity of air per time unit also has an effect on the behaviour of the temperature. It is thereby possible to obtain registration of the patient's respiration.

These temperature registrations are made with the aid of temperature-sensitive resistors, so-called thermistors, semiconductor elements, thermoelements and so forth.

Thus, the present invention aims to utilise the temperature-dependent physical and electrical material properties which are inherent in pressure sensors. This makes possible the measurement of both pressure and temperature using one and the same sensor, indeed independent of one another in a certain approach, by means of suitable coupling and sensor electronics. How this can be done is described in more detail below with reference to FIG. 3.

Registrations of other pressures, eg, sound pressure as generated by snoring sounds and heart sounds, are included in these pressure and temperature registrations, and, in addition, it is possible to measure the internal body temperature.

The advantages of being able to register these parameters inside the body, instead of outside, as mentioned above, are primarily that the patient does not have the unpleasantness of having sensors suspended from his body with the danger that these will be displaced or disturbed owing to some external action. Furthermore, it is possible to differentiate between respiration through the nose and mouth, which may be of great significance in assessing the situation. And last but not least, the signals obtained are more distinct which makes for greater accuracy in the diagnosis.

The pressure sensors are commercially available in the form of micro-tip-pressure catheters. These micro-tip-pressure catheters may optionally be temperature-compensated, but are not necessarily compensated.

Usually, pressure sensors made of silicon are used with indiffused resistors and these resistors are usually connected in a so-called Wheatstone bridge as a whole or half bridge of a known type per se. A bridge connection of this type is illustrated in FIG. 3.

Figure 3:
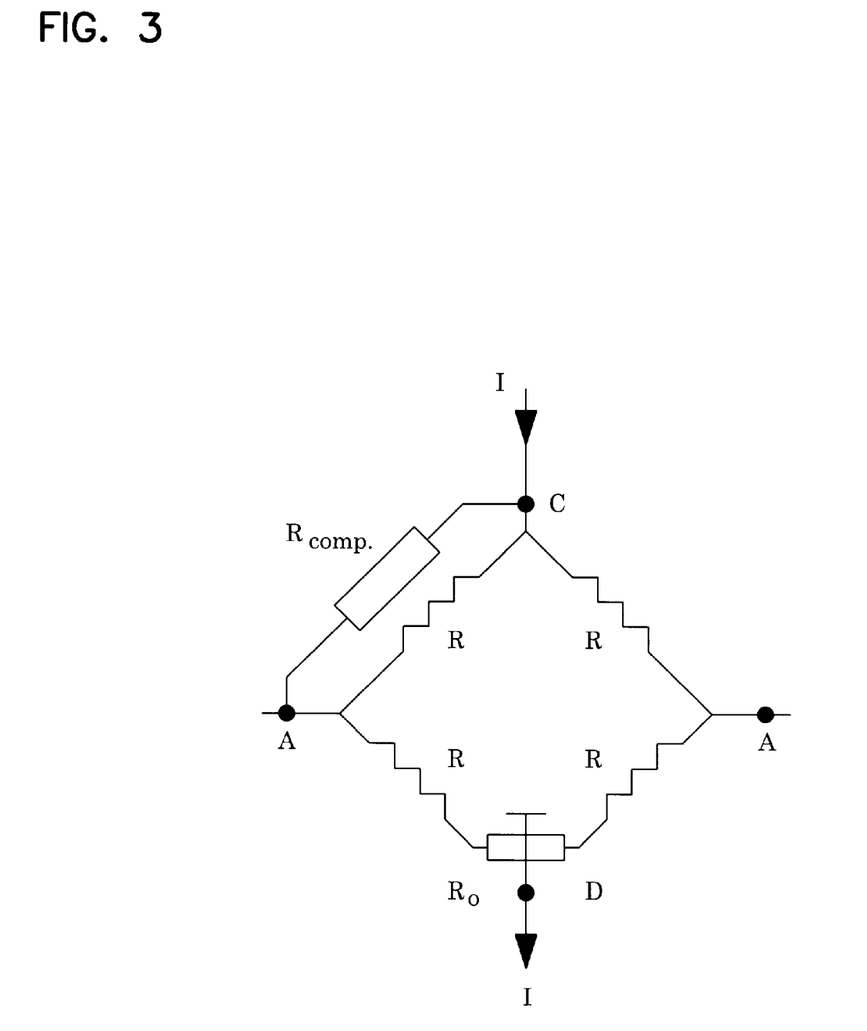
FIG. 3 illustrates a Wheatstone bridge used as a pressure and fluid flow sensor.

In FIG. 3, R denotes pressure sensor resistors, $R_{comp}$ a temperature-compensating resistor and $R_0$ a zero point adjustment resistor.

The letter I is used to denote the sensor excitation current.

The Wheatstone sensor bridge connection works with four active sensor resistors or two active sensor resistors and two passive resistors.

With the current/voltage supply at points C and D, a pressure signal can be obtained across points A and B and a fluid flow signal across points C and D (see FIG. 2) in a preferred embodiment. However, it would not be beyond the scope of the invention if this were done in other possible ways.

Furthermore, the effect of temperature is a known physical effect and the temperature coefficient for the resistors used is about 0.2%/° C., without this value being of any crucial importance to the principle.

This effect has a high degree of stability, which means great advantages with a view to obtaining usable signals and registrations chiefly of respiration, but also registrations of other forms of gas and liquid flows.

What is claimed is:

1. A method for measuring respiratory air pressure, respiratory air flow and other physiological parameters in a living body by utilization of just one sensor, the method comprising:

positioning a tube in an internal respiratory passageway of the living body in at least one position, the tube comprising a sensor positioned therein, the tube being positioned in order to locate the sensor within the respiratory passageway of the living body and exposing the sensor to pressure and flow of a medium flowing through the respiratory passageway, the sensor being capable of pressure measurements, and the sensor having temperature sensitive characteristics and capable of providing electrical signals in response to pressure and air flow thereon; and measuring the respiratory air pressure, the respiratory air flow and optionally at least one other physiological parameter in the living body using the sensor;

wherein, the measurements of the respiratory air pressure, the respiratory air flow and the optional other physiological parameter are made independently of each other and simultaneously using said sensor, the sensor providing at least a pressure signal in response to the respiratory air pressure, at least a flow signal in response to the respiratory air flow and optionally at least another signal in response to the other physiological parameter.

2. The method of claim 1, wherein the other physiological parameter is anyone of a snoring sound, a heart beat sound or a heart beat frequency, or temperature.

3. The method of claim 1, wherein the sensor is a piezoresistive sensor.

4. The method of claim 1, wherein the tube contains more than one said sensor in order to measure said parameters in several positions of the respiratory passageway.

5. A method for measuring respiratory air pressure, respiratory air flow and other physiological parameters in a living body by utilization of just one senor, the sensor being a pressure sensor comprising indiffused electrical resistors suitable for pressure measurements, and the one pressure sensor having pressure and temperature sensitive characteristics and capable of providing electrical signals in response to pressure and temperature thereon; and measuring the respiratory air pressure, the respiratory air flow and optionally at least one other physiological parameter in the living body using the sensor, wherein the measurements of respiratory air pressure, the respiratory air flow and the optional other physiological parameter are made using the one sensor, the sensor providing at least a pressure signal in response to the respiratory air pressure, at least a flow signal in response to the respiratory air flow, and optionally at least another signal in response to the other physiological parameter.

* * * * *

UNITED STATES PATENT AND TRADEMARK OFFICE
CERTIFICATE OF CORRECTION

PATENT NO. : 6,216,702 B1
DATED : April 17, 2001
INVENTOR(S) : Gjersoe

It is certified that error appears in the above-identified patent and that said Letters Patent is hereby corrected as shown below:

Title page,
The title page showing the illustrative figure should be deleted and replaced with the attached title page.

Drawings,
Sheet 1 and 3, consisting of Figs. 1 and 3, should be deleted and substitute therefor the corrected drawing Figs. 1 and 3, as shown on the attached pages.

Column 4,
Line 48, "senor" should read -- sensor --.

Signed and Sealed this

Eleventh Day of June, 2002

*Attest:*

*Attesting Officer*

JAMES E. ROGAN
*Director of the United States Patent and Trademark Office*

(12) United States Patent
Gjersøe (10) Patent No.: US 6,216,702 B1
(45) Date of Patent: *Apr. 17, 2001

(54) INTERNAL REGISTRATION OF GAS/AIR— AND OTHER FLUID FLOWS IN A HUMAN BODY AND USE OF PRESSURE SENSORS FOR SUCH REGISTRATION

(75) Inventor: Bjørn G. Gjersøe, Høvik (NO)

(73) Assignee: Camtech AS, Høvik (NO)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/864,787

(22) Filed: May 29, 1997

Related U.S. Application Data (63) Continuation of application No. PCT/NO95/00230, filed on Dec. 12, 1995.

(30) Foreign Application Priority Data

Dec. 14, 1994 (NO) ........................................ 944844

(51) Int. Cl.$^7$ .................................................. A61B 19/00
(52) U.S. Cl. ............... 128/898; 128/200.24; 128/205.23; 600/532; 600/538
(58) Field of Search ...................... 128/897, 898, 128/200.24, 200.22, 205.23; 600/529, 532, 538

(56) References Cited

U.S. PATENT DOCUMENTS

| | | | |
|---|---|---|---|
| 3,672,352 | * 6/1972 | Summers | 128/2 |
| 3,961,626 | * 6/1976 | Houchen et al. | 128/145 R |
| 4,554,927 | 11/1985 | Fussell . | |
| 4,938,212 | * 7/1990 | Snook et al. | 128/205.24 |
| 5,056,519 | * 10/1991 | Vince | 128/419 |
| 5,311,875 | 5/1994 | Stasz . | |
| 5,339,051 | * 8/1994 | Koehler et al. | 331/65 |
| 5,540,220 | * 7/1996 | Gropper et al. | 128/204.23 |
| 5,680,871 | * 10/1997 | Ganshorn | 128/720 |
| 5,833,603 | * 11/1998 | Kovacs et al. | 600/317 |
| 5,836,989 | * 11/1998 | Shelton | 607/27 |

FOREIGN PATENT DOCUMENTS

| | | |
|---|---|---|
| 57746/94 | 9/1994 | (AU) . |
| 0 046 570 | 3/1982 | (EP) . |
| 0 392 897 | 10/1990 | (EP) . |
| 1 313 486 | 4/1973 | (GB) . |
| 377 276 | 6/1975 | (SE) . |
| 377276 | 6/1975 | (SE) . |

OTHER PUBLICATIONS

Cranen, et al. "Pressure measurements during speech production using semiconductor miniature pressure transducers: Impact on models for speech production." *J. Acoust. Soc. Am.* 77(4), Apr. 1985. pp. 1543–1551.

(List continued on next page.)

*Primary Examiner*—Dinh X. Nguyen
(74) *Attorney, Agent, or Firm*—Merchant & Gould P.C.

(57) ABSTRACT

A method for internal registration of the flow of a fluid into, in or out of a living body wherein one or a series of sensors are placed at one or more points along the flow path of the fluid and the registration takes place through the utilisation of the sensor's or sensors' inherent, pressure and/or temperature—dependent physical and electrical properties, by measuring the temperature and the difference in temperature in the flowing fluid.

5 Claims, 3 Drawing Sheets

FIG. 1

FIG. 3